United States Patent
Atzinger et al.

(10) Patent No.: US 9,986,958 B2
(45) Date of Patent: Jun. 5, 2018

(54) MEDICAL EXAMINATION AND/OR TREATMENT APPARATUS

(71) Applicants: Michael Atzinger, Seybothenreuth (DE); Stefan Groß, Trabitz (DE); Norbert Herrmann, Ebnath (DE)

(72) Inventors: Michael Atzinger, Seybothenreuth (DE); Stefan Groß, Trabitz (DE); Norbert Herrmann, Ebnath (DE)

(73) Assignee: Siemens Aktiengesellschaft, München (DE)

( * ) Notice: Subject to any disclaimer, the term of this patent is extended or adjusted under 35 U.S.C. 154(b) by 0 days. days.

(21) Appl. No.: 14/718,851

(22) Filed: May 21, 2015

(65) Prior Publication Data

US 2015/0335387 A1    Nov. 26, 2015

(30) Foreign Application Priority Data

May 21, 2014    (DE) .................. 10 2014 209 684

(51) Int. Cl.
| | |
|---|---|
| *A61B 19/00* | (2006.01) |
| *A61B 6/00* | (2006.01) |
| *F16G 13/16* | (2006.01) |
| *H02G 11/00* | (2006.01) |
| *H05G 1/02* | (2006.01) |
| *B25J 19/00* | (2006.01) |
| *B25J 18/02* | (2006.01) |

(52) U.S. Cl.
CPC .............. *A61B 6/4441* (2013.01); *A61B 6/56* (2013.01); *B25J 19/0025* (2013.01); *F16G 13/16* (2013.01); *H02G 11/00* (2013.01); *H02G 11/006* (2013.01); *H05G 1/02* (2013.01); *B25J 18/025* (2013.01)

(58) Field of Classification Search
None
See application file for complete search history.

(56) References Cited

U.S. PATENT DOCUMENTS 2,595,260 A * 5/1952 Hollstein ............. A61B 6/0457
                                                                       248/324
3,118,066 A * 1/1964 Thomas ............... A61B 6/4464
                                                                       378/194

(Continued)

FOREIGN PATENT DOCUMENTS

| CN | 102028486 A | 4/2011 |
|---|---|---|
| CN | 102256427 A | 11/2011 |

(Continued)

OTHER PUBLICATIONS

U.S. Appl. No. 61/754,214 retrieved from https://patentscope.wipo.int/.*

(Continued)

*Primary Examiner* — Michael Logie
(74) *Attorney, Agent, or Firm* — Lempia Summerfield Katz LLC

(57) ABSTRACT

A medical examination and/or treatment apparatus includes a robot with a multiaxially movable arm, a C-arm mounted on the multiaxially movable arm, a cable strand for supplying the C-arm, and a device for guiding the cable strand in a movement of the C-arm. The device for guiding the cable strand is arranged at or on the robot or a component of the robot.

13 Claims, 6 Drawing Sheets

(56) References Cited

U.S. PATENT DOCUMENTS

| | | | | |
|---|---|---|---|---|
| 4,114,043 A * | 9/1978 | Gansfried | ............... | A61B 6/56 174/69 |
| 4,720,143 A * | 1/1988 | Schwartz | ............... | B60N 2/10 296/65.06 |
| 4,901,339 A * | 2/1990 | Heinz | ............... | F16M 11/26 248/332 |
| 4,907,768 A * | 3/1990 | Masseron | ............ | B66F 11/048 212/197 |
| 5,450,466 A * | 9/1995 | Kadowaki | ............ | A61B 6/4405 378/189 |
| 5,475,730 A * | 12/1995 | Galando | ............. | A61B 6/4405 378/157 |
| 6,431,751 B1 | 8/2002 | Everett | ............... | A61B 6/4233 378/193 |
| 6,491,430 B1 * | 12/2002 | Seissler | ............... | A61B 6/4405 348/E5.086 |
| 6,684,731 B1 * | 2/2004 | Karlinger | ............ | B25J 19/0025 248/51 |
| 7,604,403 B2 * | 10/2009 | Yi | ............................ | A61B 6/56 378/193 |
| 8,117,939 B2 | 2/2012 | Burlot | | |
| 8,662,748 B2 | 3/2014 | Herrmann et al. | | |
| 8,769,922 B2 | 7/2014 | Rijken et al. | | |
| 9,289,902 B2 | 3/2016 | Groβ et al. | | |
| 9,512,912 B1 * | 12/2016 | Edsinger | ............... | F16H 48/12 |
| 9,659,427 B2 * | 5/2017 | Stinson | ................... | G07F 11/42 |
| 2004/0041321 A1 | 3/2004 | Hsieh | | |
| 2008/0164382 A1 * | 7/2008 | Burlot | ................. | B25J 19/0025 248/74.2 |
| 2008/0247516 A1 * | 10/2008 | Fink | .................... | A61B 6/4464 378/194 |
| 2009/0154652 A1 * | 6/2009 | Yi | ....................... | A61B 6/4464 378/194 |
| 2009/0166478 A1 | 7/2009 | Choi | | |
| 2010/0150317 A1 * | 6/2010 | Herrmann | ........... | A61B 6/4441 378/194 |
| 2011/0072931 A1 * | 3/2011 | Gro | ......................... | A61B 6/56 74/490.02 |
| 2011/0249804 A1 * | 10/2011 | Wendlandt | ............ | A61B 6/447 378/198 |
| 2012/0085078 A1 * | 4/2012 | Rijken | ................. | H02G 3/0475 59/78.1 |
| 2012/0121071 A1 * | 5/2012 | Herrmann | ................ | A61B 6/56 378/194 |
| 2012/0275571 A1 * | 11/2012 | Neuber | ................ | A61B 6/4441 378/194 |
| 2013/0015300 A1 * | 1/2013 | Klinke | ................... | A61G 7/018 248/49 |
| 2013/0037504 A1 * | 2/2013 | Graves | ................... | A47H 1/022 211/124 |
| 2013/0322990 A1 * | 12/2013 | Chen | ................... | H01L 21/6773 414/217 |
| 2014/0033851 A1 | 2/2014 | Hermey et al. | | |
| 2015/0328780 A1 * | 11/2015 | Burlot | ................. | B25J 19/0025 74/490.02 |
| 2017/0023154 A1 * | 1/2017 | Jaeker | ................... | H02G 3/0468 |

FOREIGN PATENT DOCUMENTS

| | | | | |
|---|---|---|---|---|
| CN | 102460871 A | | 5/2012 | |
| CN | 102463575 A | | 5/2012 | |
| CN | 102639029 A | | 8/2012 | |
| DE | 10141366 A1 | * | 10/2002 | ......... B25J 19/0025 |
| DE | 10141366 A1 | | 10/2002 | |
| DE | 102006028145 A1 | | 12/2007 | |
| DE | 102007018543 A1 | | 10/2008 | |
| DE | 202006020499 U1 | | 11/2008 | |
| DE | 102009043448 A1 | | 4/2011 | |
| DE | 202011004786 U1 | | 7/2011 | |
| DE | 102010019269 A1 | | 11/2011 | |
| DE | 202012004601 | * | 6/2012 | ............... A61B 6/44 |
| JP | 2012161903 A | * | 8/2012 | ........... B23K 11/115 |
| WO | WO 2011025081 A1 | * | 3/2011 | ......... B25J 19/0025 |
| WO | WO 2014111500 A1 | * | 7/2014 | ......... B25J 19/0025 |

OTHER PUBLICATIONS

Translation of Burlot U.S. Appl. No. 61/754,214.*
Loop1. (2007). In R. E. Allen (Ed.), The penguin English Dictionary (3rd ed.). London, UK: Penguin. Retrieved from http://search.credoreference.com/content/entry/penguineng/loop1/0.*
German Office Action for related German Application No. 10 2014 209 684.7, dated Apr. 20, 2015, with English Translation.
Chinese Office Action for related Chinese Application No. 201510261202.6 dated Dec. 23, 2016, with English Translation.

* cited by examiner

MEDICAL EXAMINATION AND/OR TREATMENT APPARATUS

This application claims the benefit of DE 10 2014 209 684.7, filed on May 21, 2014, which is hereby incorporated by reference in its entirety.

BACKGROUND

The present embodiments relate to a medical examination and/or treatment apparatus.

A medical examination and/or treatment apparatus is produced by Siemens AG under the name "ARTIS Zeego." The ARTIS Zeego is a robot that may be used for angiography procedures. The robot includes a multiaxially movable robot arm that carries a C-arm. The cable strand attached to the C-arm contains data lines, control lines, and lines for supplying current. In this conventional medical apparatus, the robot arm has several passages through which the cable strand is guided. The cable strand ends in a cable storage device that may be mounted on a ceiling. During a movement of the robot, the length of the cable strand increases, such that the cable strand is pulled out of the cable storage device. When the C-arm of the robot is then moved back again to a starting position, the cable strand is drawn back into the cable storage device under the influence of a spring element.

Since a medical examination and/or treatment apparatus of this kind has more possible movements than an industrial robot, it may be difficult to guide the cable strand accordingly.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a medical examination and/or treatment apparatus that permits further possible movements of the C-arm is provided.

In a medical examination and/or treatment apparatus, according to one or more of the present embodiments, a device (e.g., a guide) is arranged at or on a robot or a component of the robot.

The cable storage device, which is arranged on the ceiling in conventional apparatuses, is replaced by a device that is arranged at or on the robot or at or on a component of the robot. The device is configured to guide a cable strand in a movement of a C-arm and is configured to make a greater required length of the cable strand available. In this way, the cable storage device may be dispensed with, since the required additional length of the cable strand may be made available directly at the robot. This provides the advantage that the cable strand may be guided in all conceivable movements about the several axes without being restricted by a ceiling-mounted cable storage device or a ceiling-mounted cable drum. A further advantage is that the cable strand, or the additional length thereof required for the movement, may be moved more rapidly, such that the speed of movement of the multiaxially movable robot arm may also be increased. The additional length of the cable strand required during a movement is no longer made available in a ceiling-mounted cable storage device, but instead, is made available directly at the robot (e.g., at the multiaxially movable robot arm).

According to a first embodiment, the guide is configured as a telescopic pull-out system with one or more pull-outs. In the simplest case, the telescopic pull-out system has just one pull-out that is linearly movable. As a result of this, the cable strand may be guided in a movement of the C-arm. The actuation of the pull-out of the telescopic pull-out system provides the required guiding of the cable strand, which is to be provided during a movement of the C-arm. To further improve guiding, according to one or more of the present embodiments, the telescopic pull-out system may include a plurality of pull-outs. For example, the telescopic pull-out system may include two or three pull-outs that are movable relative to one another. One pull-out is mounted on the robot or on an articulated arm of the robot, while another pull-out is connected to the cable strand.

For increased user-friendliness, at least one pull-out of the telescopic pull-out system may have a drive. The telescopic pull-out system may be driven by the drive. As a result of this, an adjustment of the medical examination and/or treatment apparatus may take place automatically. According to a development, all the pull-outs of the telescopic pull-out system may include a drive. In one embodiment, two or more pull-outs are coupled kinematically to each other, such that when one pull-out is actuated, another pull-out or a plurality of other pull-outs is/are likewise actuated (e.g., moved). With this measure, the speed of movement of the telescopic pull-out system and therefore the speed of movement of the cable strand may be increased.

In the context of one or more of the present embodiments, the drive may be configured as a rotating motor, a linear motor, a motor unit with a draw spindle, a hydraulic cylinder, or a pneumatic cylinder. All of these drives are able to move the telescopic pull-out system.

According to one embodiment, the telescopic pull-out system includes a counterweight that, in the event of a movement of the telescopic pull-out system, is movable in a direction counter to the movement. Using the counterweight, a mass balance is achieved. As a result of this, excessively high forces in the cable strand may be avoided. For example, using the counterweight, the weight may be compensated according to a tilt angle. In one embodiment, each pull-out of a plurality of pull-outs of a telescopic pull-out system may be provided with a counterweight. The counterweight always moves in the opposite direction in relation to the telescopic pull-out system or the pull-out thereof. As a result of this, the modified weight distribution is automatically compensated by the retraction or extension of a pull-out.

In this connection, the counterweight is coupled to the telescopic pull-out system via a pulling device. The pulling device may be configured as a belt or chain such that, when the pull-out moves, the counterweight is also moved by the kinematic coupling provided by the pulling device. In an opposite movement (e.g., when the pull-out is drawn in to a retracted position), the counterweight is likewise moved in the opposite direction.

In one embodiment, in the medical examination and/or treatment apparatus, at least one pull-out of the plurality of pull-outs of the telescopic pull-out system includes a rotating pulling device that is coupled on one side to a first pull-out and is coupled on the opposite side to a second pull-out. The pulling device may, for example, be configured as a continuous belt that runs over two rollers spaced apart from each other. One pull-out may be located on the upper side, while the counterweight may be located on the lower side.

In a further variant, the telescopic pull-out system may be assigned a damping element in order to damp a movement of the pull-outs. The aim is to damp any undesired oscillations or vibrations that may otherwise have a disadvantageous effect in an imaging apparatus. The damping element may be configured as a viscous damper, for example.

It is also within the context of one or more of the present embodiments that the telescopic pull-out system has one or more damped limit stops. In this way, mechanical jolts or shocks are avoided when a pull-out reaches a limit stop. This measure also makes it possible to avoid disturbances in an imaging apparatus.

In the telescopic pull-out system that has several pull-outs, all of the pull-outs may be actuated in synchrony. In this way, the position of the cable strand may be determined at any time.

According to an alternative configuration, the guide may be configured as a joint with at least two joint portions. Instead of the telescopic pull-out system, a joint that is connected to the robot (e.g., to a robot arm) and to the cable strand is therefore provided. The at least two joint portions are rotatable relative to each other in a movement plane, such that the distance between their free ends can be modified between practically zero and the entire length of the two joint portions. Since the cable strand is connected to one end of this joint, the cable strand may be guided by movement of the joint. When the C-arm is moved by a movement of the multiaxially movable robot arm, which may have several articulated movable portions, the cable strand may thus be guided by a corresponding movement of the joint having at least two joint portions. If appropriate, the joint may also have more than two joint portions (e.g., three or four joint portions). As a result of this, a scissor-like joint or a zigzag joint is formed. However, by choosing a joint with joint portions of matching length, the required guiding of the cable strand may also be provided by a joint that has two joint portions.

In one embodiment, in the medical examination and/or treatment apparatus, the joint includes at least one spring element for generating a return force. After the movement of the joint to a deflected position, the spring element may draw the joint, or the joint portions thereof, back to a starting position. The joint may, for example, be stopped in the deflected state.

To increase user-friendliness, the joint may include at least one drive. Analogously to the described drive of the telescopic pull-out system, the drive for the joint may be configured as a rotating motor, a linear motor, a motor unit with a draw spindle, a hydraulic cylinder, or a pneumatic cylinder.

In both variants (e.g., in the telescopic pull-out system and also in the joint), the cable strand may be arranged on the guide with the aid of at least one holder. In one case, the holder may thus be mounted on the telescopic pull-out system, while in the other case, the holder may be arranged on the joint.

The cable strand of the medical examination and/or treatment apparatus may be accommodated in a hose or in a sheath. Since the hose or the sheath does not touch any other components of the apparatus, practically no wear occurs. This is advantageous for use in a sterile treatment room. A further advantage is that the cable strand accommodated in the hose or in the sheath may be easily cleaned if necessary. This provides that all the hygiene requirements associated with a use in a medical environment are satisfied.

DETAILED DESCRIPTION

Figure 1:
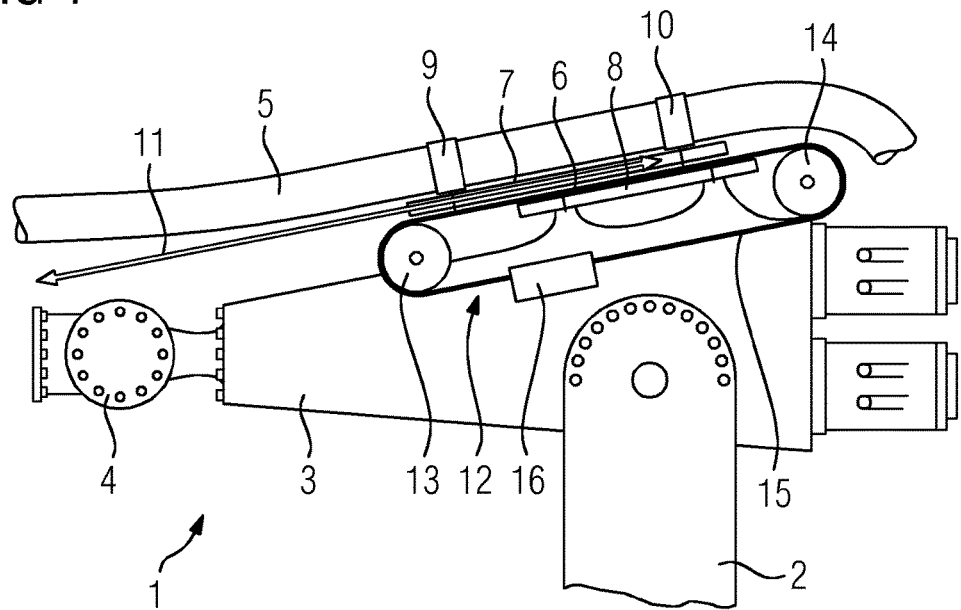
FIG. 1 shows a detail of a first embodiment of a medical examination and/or treatment apparatus.

FIG. 1 shows a detail of one embodiment of a medical examination and/or treatment apparatus 1 that includes a robot 2 (of which only part is shown), on which a multi-axially movable robot arm 3 is mounted. The articulated movable robot arm 3 carries, at a free end, a C-arm 4 that is a component part of an angiography apparatus. FIG. 1 shows that the medical examination and/or treatment apparatus 1 has a cable strand 5, of which a portion is shown. The cable strand 5 is connected to the C-arm 4 and to the robot 2. In a movement of the multiaxially movable C-arm 4, the cable strand 5 is to be guided accordingly in this movement, without appreciable tensile stresses thereby occurring. The cable strand 5 contains a cable bundle that includes data lines, control lines, and power supply lines for supplying the C-arm 4.

As a way for guiding the cable strand 5 in a movement of the C-arm, a telescopic pull-out system 6 (e.g., a guide) that is arranged on the robot 2 or on the arm 3 of the robot 2 is used.

In the embodiment shown, the telescopic pull-out system 6 includes two pull-outs 7, 8. The pull-out 7 is fixedly connected to the cable strand 5 by holders 9, 10. The pull-out 8 is arranged stationary on the robot arm 3. Modified configurations in which the pull-out 8 is arranged to be movable with respect to the robot arm 3 may also be provided.

The telescopic pull-out system 6 includes a drive (not shown), by which the pull-out 7 is linearly movable with respect to the pull-out 8. The direction of movement of the pull-out 7 is indicated by the double arrow 11.

Another component part of the telescopic pull-out system 6 is a belt drive 12 including two deflecting rollers 13, 14 that are spaced apart from each other, are rotatably mounted on the robot arm 3, and are coupled to each other by a belt 15. The continuous belt 15 loops around the two deflecting rollers 13, 14. An upper side of the belt 15 is fixedly connected to the pull-out 7. A lower side of the belt 15 includes a counterweight 16, such that, when the pull-out 7 moves in one direction, the counterweight 16 is moved in the opposite direction. The counterweight 16 permits a mass balance, which provides the advantage that the actuating forces used to move the pull-out 7 are not unnecessarily high.

During a movement of the C-arm 4, the cable strand 5 may thus be guided correspondingly by a movement of the telescopic pull-out system 6, such that the cable strand 5 may follow each movement of the C-arm 4.

Figure 2:
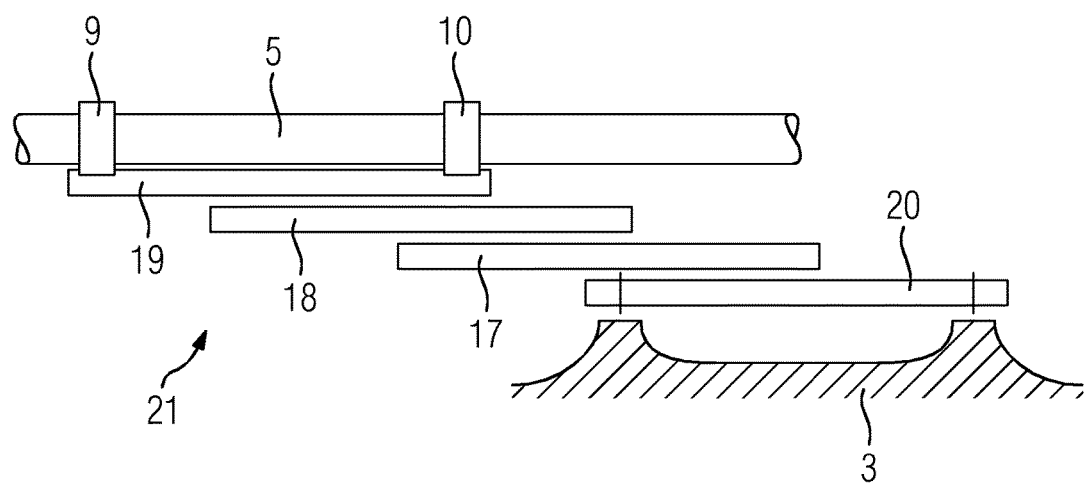
FIG. 2 shows a schematic view of one embodiment of a telescopic pull-out system.

FIG. 2 shows a detail of a further embodiment of a medical examination and/or treatment apparatus with a telescopic pull-out system 21. In contrast to the previous illustrative embodiment, the robot arm 3 includes a total of three movable pull-outs 17, 18, 19, of which the pull-out 17 shown at the lowermost position in FIG. 2 is movable relative to a stationary guide 20. In line with the previous illustrative embodiment, the pull-out 19 is connected to the cable strand 5 via holders 9, 10. By comparison with the previous illustrative embodiment, the telescopic pull-out system 21 shown in FIG. 2 has the advantage that the same pull-out distance is achieved with a smaller length of the individual pull-outs 17, 18, 19.

Figure 3:
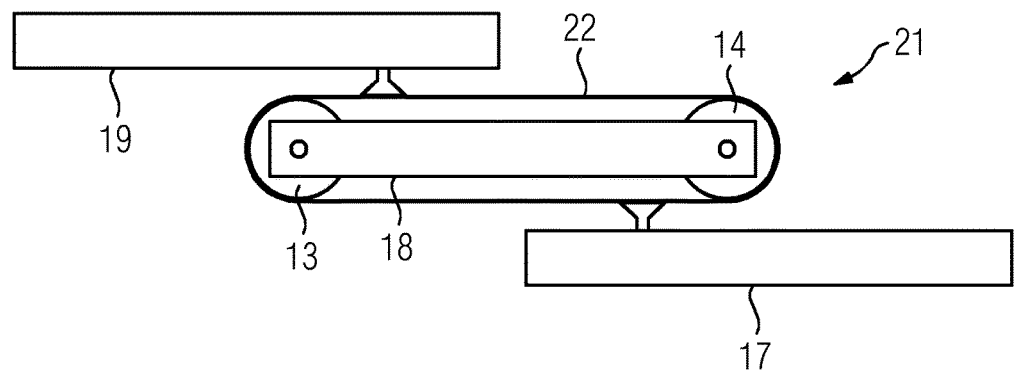
FIG. 3 shows a further schematic view of one embodiment of a telescopic pull-out system.

FIG. 3 shows the pull-outs 17, 18, 19 of the telescopic pull-out system 21. The pull-out 18 has deflecting rollers 13, 14 that are coupled to each other kinematically by a core 22. FIG. 3 shows that the pull-out 18 is coupled via an upper side to the pull-out 19 and is coupled via a lower side to the pull-out 17. Using this kinematic coupling, the pull-outs 17, 19 are controlled such that the pull-outs 17, 19 move relative to each other in synchrony.

Figure 4:
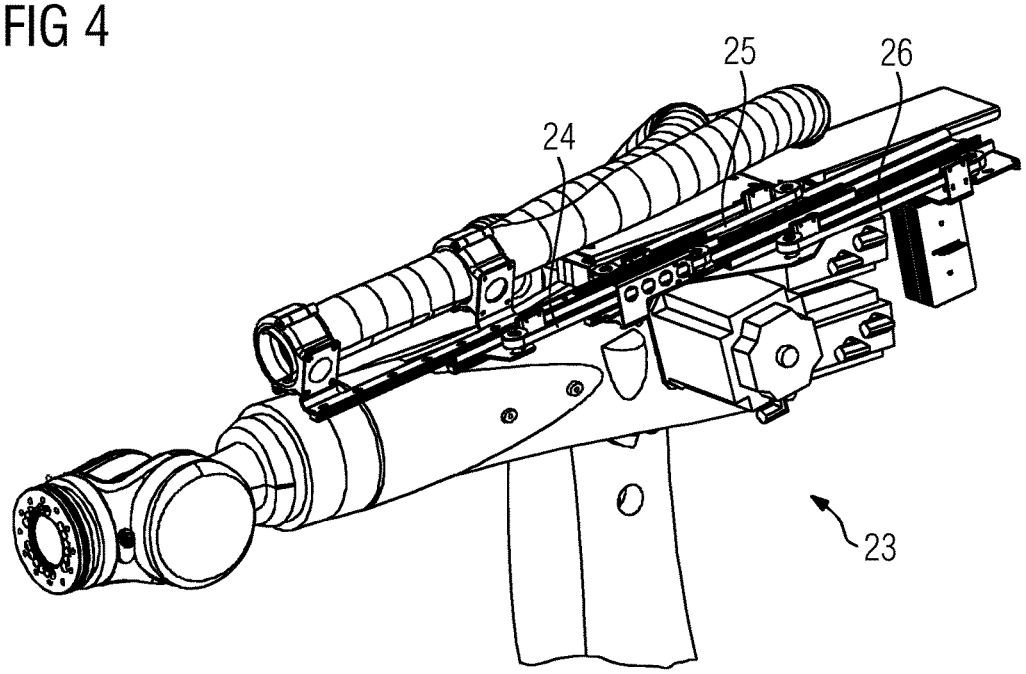
FIGS. 4-6 show an illustrative embodiment of a medical examination and/or treatment apparatus with a telescopic pull-out system.
Figure 5:
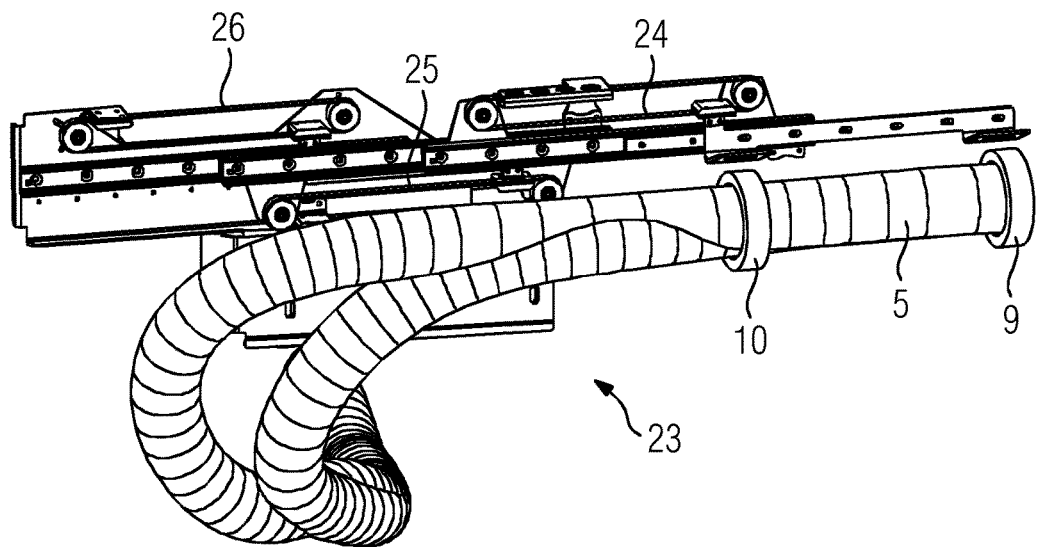

FIG. 4 shows a further embodiment of a telescopic pull-out system 23 including a first belt drive 24, a second belt drive 25, and a third belt drive 26. FIG. 5 shows another perspective of the telescopic pull-out system 23 shown in FIG. 4. The holders 9, 10 for the cable strand 5 are connected to a component of the first belt drive 24. The first belt drive 24 is connected to the second belt drive 25, which is connected to the third belt drive 26. The triple telescopic pull-out system 23 is driven by motor. As a result of this, the forces in the cable strand 5 are largely eliminated. The telescopic pull-out system 23 may be controlled such that only a single belt drive is driven. As a result of this, the movement of the cable strand 5 is transmitted in the ratio 1:3. As a result of this, the distance traveled is trebled. One of the belt drives may, for example, be driven linearly, or the telescopic pull-out system 23 may alternatively be driven by one of the illustrated deflecting rollers, which is provided with a drive. Since the individual pull-outs are coupled to one another kinematically via the belt drives, it is immaterial at which location the drive is effected, since all the components of the telescopic pull-out system 23 are moved.

Figure 6:
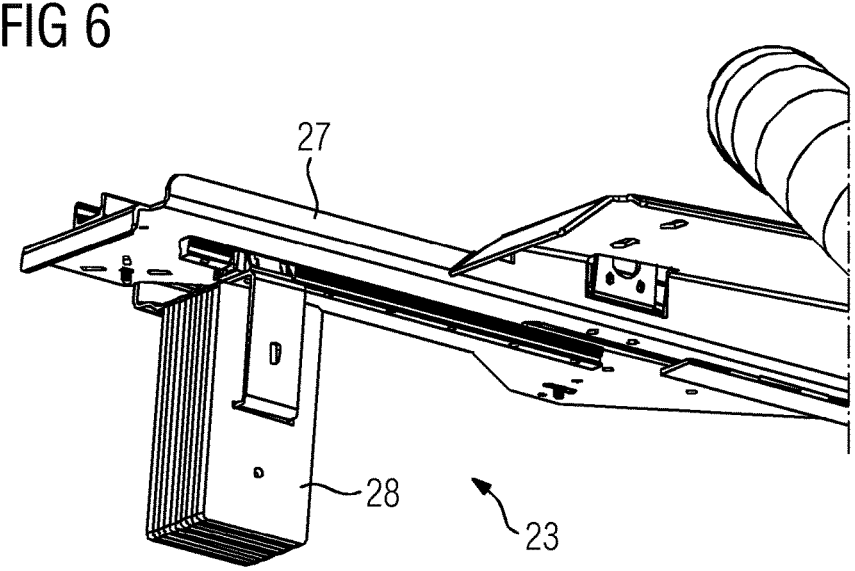

FIG. 6 shows a detail of one embodiment of the telescopic pull-out system 23 shown in FIGS. 4 and 5, with a counterweight 28 mounted on a pull-out 27. The counterweight 28 may be moved by the pull-out 27 in order to provide the required mass balance or a reduction of the return force.

Figure 7:
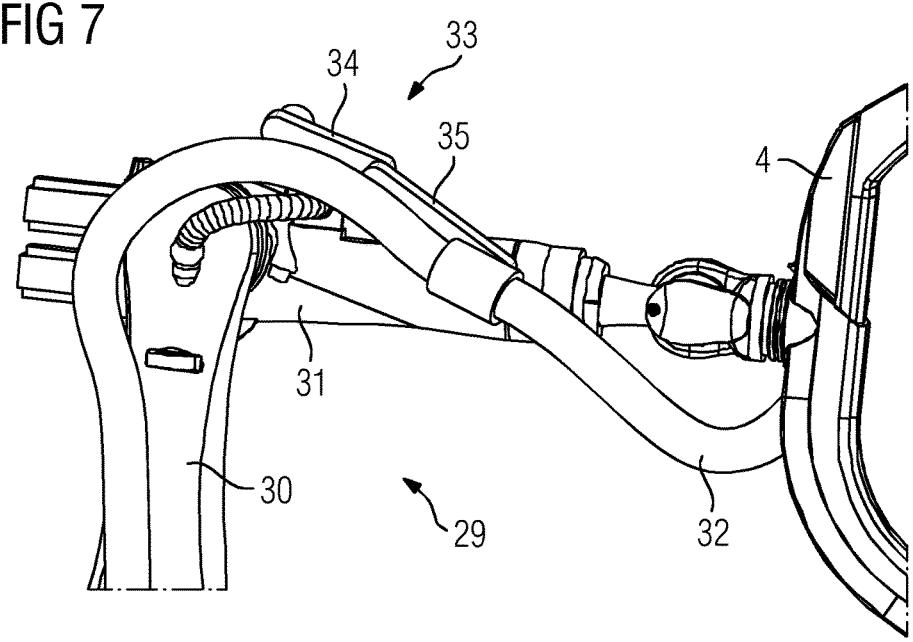
FIGS. 7-12 show a further illustrative embodiment of a medical examination and/or treatment apparatus, in which a cable strand may be guided by a joint.
Figure 8:
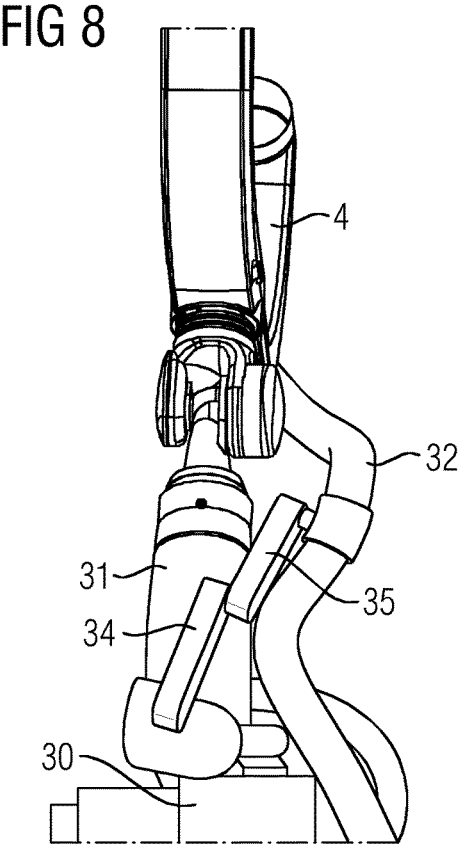
Figure 9:
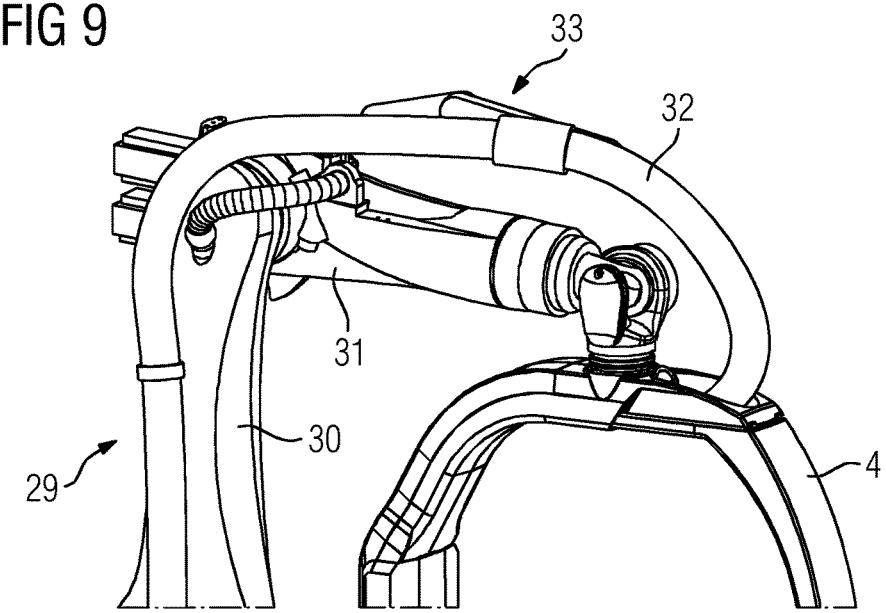

FIGS. 7 to 12 show a further embodiment of a medical examination and/or treatment apparatus 29 that, in line with the previous illustrative embodiments, has a robot 30 with a multiaxially movable robot arm 31, on which a C-arm 4 is mounted so as to be movable about several axes. A joint 33 with two joint portions 34, 35 serves as the means for guiding a cable strand 32. The joint 33 is mounted on the arm 31 of the robot 30. The joint portion 34 is connected to the robot arm 31, and the joint portion 35 is connected to the cable strand 32. In the case of a movement of the arm 31 of the robot 30 and/or a movement of the C-arm 4 relative to the robot arm 31, the cable strand 32 may be correspondingly guided by the joint 33, such that the required length of the cable strand 32 may be made available in every position. FIGS. 7 and 8 show the joint 33 in an end position in which the two joint portions 34, 35 are oriented almost parallel. In this position, the end of the joint portion 35 directed toward the C-arm 4 is especially close to the C-arm. FIG. 9 shows the medical examination and/or treatment apparatus 29 from another perspective.

Figure 10:
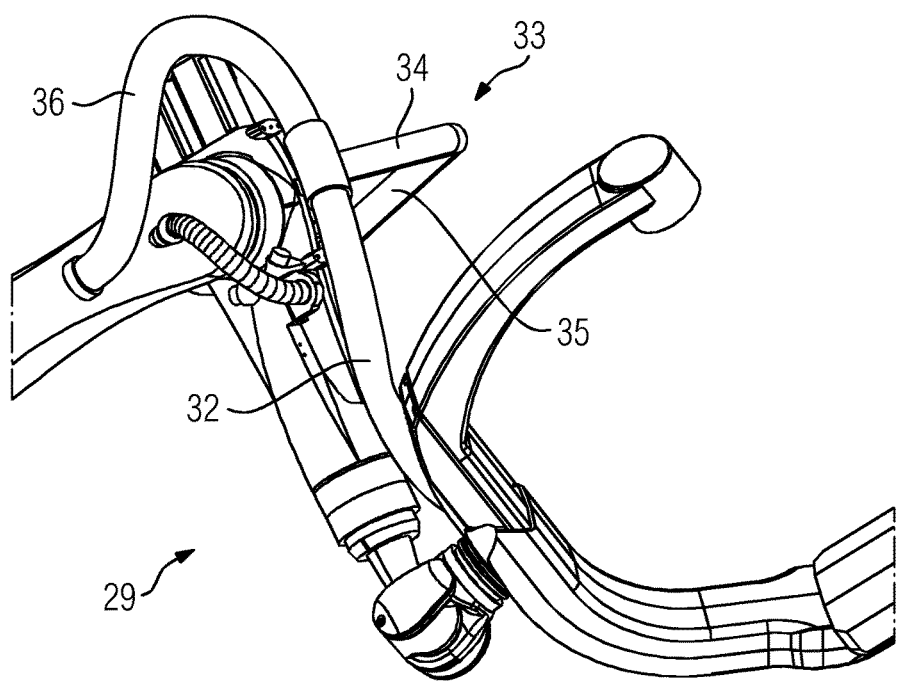

FIG. 10 shows the apparatus 29 in a position in which the joint 33 is drawn in (e.g., the two joint portions 34, 35 enclose an acute angle). Accordingly, in comparison with the previous figures, the cable strand 32 is located in a retracted position, which may also be seen from the loop 36 that is formed. A movement or adjustment of the joint 33 takes place by an electric drive motor that is arranged at the coupling site between the two joint portions 34, 35.

Figure 11:
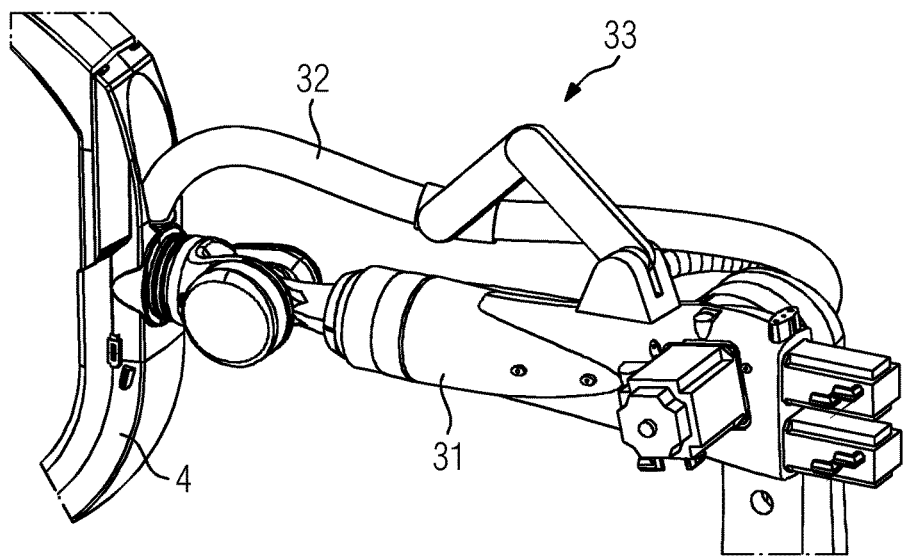
Figure 12:
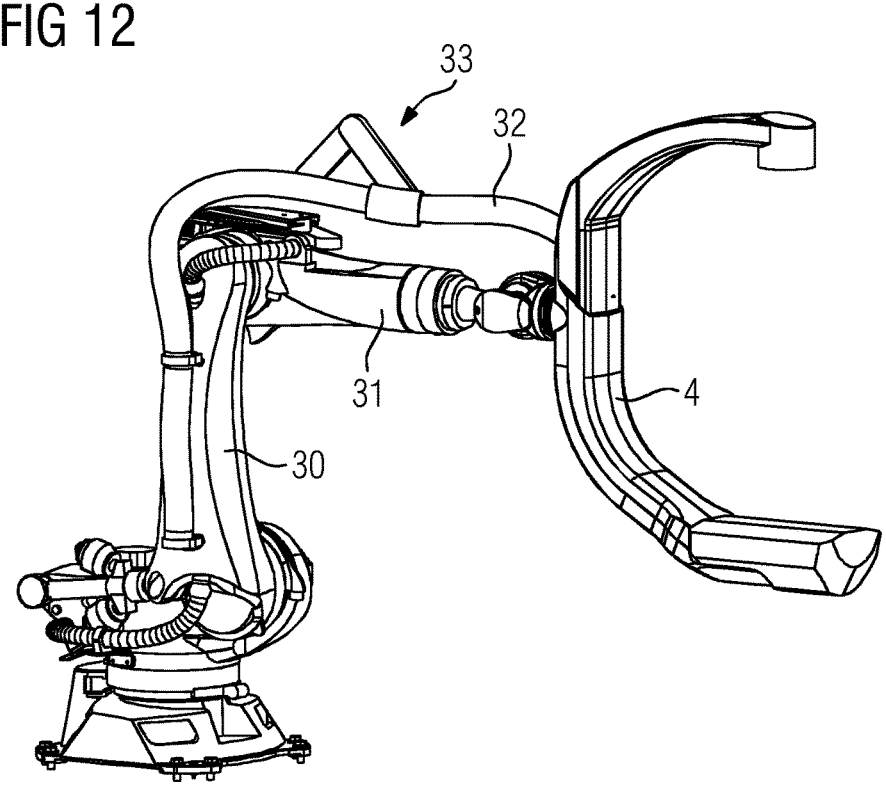

FIGS. 11 and 12 show the joint 33 in an intermediate position between the fully retracted position shown in FIG. 10 and the fully extended position shown in FIGS. 7 to 9. FIG. 11 is a detail view of FIG. 12 from the opposite side.

FIGS. 11 and 12 show that the cable strand 32 may be moved along a fixed path by suitable control of the driven joint 33. Depending on the position of the joint 33, the cable strand 32 may be moved toward or away from the C-arm. The cable strand 32, which has a sheath, may be easily cleaned, such that the cable strand 32 meets the hygiene requirements in a medical environment.

Although the invention has been illustrated and described in detail based on illustrative embodiments, the invention is not limited by the disclosed examples. Other variations may be derived from these by a person skilled in the art, without departing from the scope of protection of the invention.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A medical examination, treatment, or examination and treatment apparatus comprising:
    a robot comprising a multiaxially movable arm;
    a C-arm mounted on the multiaxially movable arm;
    a cable strand fixedly connected to the C-arm at a first connection point and operable to supply the C-arm;
    a guide comprising at least a first portion and a second portion, the second portion being moveably connected to the first portion via at least a continuous loop; and
    a drive connected to the continuous loop;
    wherein the first portion of the guide is mounted on an external portion of the multiaxially moveable arm of the robot, and the second portion of the guide is fixedly connected to the cable strand at a second connection point that guides the cable strand along at least a portion of a length of the multiaxially movable arm,
    wherein the drive is configured to move the second portion of the guide relative to the first portion of the guide,
    wherein the continuous loop includes a belt, and
    wherein the drive includes two spaced apart rollers with the belt disposed around the two spaced apart rollers.

2. The medical examination, treatment, or examination and treatment apparatus of claim 1, wherein the first portion and the second portion of the guide are configured as a telescopic pull-out system with one or more pull-outs.

3. The medical examination, treatment, or examination and treatment apparatus of claim 2, wherein the drive is connected to at least one of the one or more pull-outs of the telescopic pull-out system.

4. The medical examination, treatment, or examination and treatment apparatus of claim 2, wherein the telescopic pull-out system comprises a counterweight that, in the event of a movement of the telescopic pull-out system, is movable in a direction counter to the movement of the telescopic pull-out system.

5. The medical examination, treatment, or examination and treatment apparatus of claim 4, wherein the counterweight is coupled to a pull-out of the one or more pull-outs via a pulling device.

6. The medical examination, treatment, or examination and treatment apparatus of claim 2, wherein the one or more pull-outs comprise a plurality of pull-outs, and
wherein at least one pull-out of the plurality of pull-outs of the telescopic pull-out system has a rotating pulling device that is coupled on one side to a first pull-out of the plurality of pull-outs and on the opposite side to a second pull-out of the plurality of pull-outs.

7. The medical examination, treatment, or examination and treatment apparatus of claim 1, wherein the drive is configured as a rotating motor, a linear motor, a motor unit with draw spindle, a hydraulic cylinder, or a pneumatic cylinder.

8. The medical examination, treatment, or examination and treatment apparatus of claim 1, wherein the cable strand is arranged on the guide with the aid of at least one holder.

9. The medical examination, treatment, or examination and treatment apparatus of claim 1, wherein the cable strand is accommodated in a hose or a sheath.

10. The medical apparatus of claim 1, wherein the other portion of the first portion and the second portion of the guide is attached to the belt.

11. The medical apparatus of claim 1, wherein the drive is connected to one of the two spaced apart rollers of the first portion or the second portion, such that the second portion of the guide moves relative to the first portion of the guide.

12. The medical apparatus of claim 1, wherein the first portion of the guide is pivotably connected to the multiaxially movable arm, and the second portion of the guide is pivotably connected to the cable strand.

13. The medical apparatus of claim 1, wherein the moveable connection of the first portion and the second portion includes a pivotable connection, and
wherein the drive includes a motor arranged at the pivotable connection.

* * * * *